United States Patent
Li et al.

(10) Patent No.: US 11,963,708 B2
(45) Date of Patent: Apr. 23, 2024

(54) LEFT ATRIAL APPENDAGE OCCLUDER AND OCCLUSION SYSTEM

(71) Applicant: LIFETECH SCIENTIFIC (SHENZHEN) CO., LTD., Guangdong (CN)

(72) Inventors: Anning Li, Shenzhen (CN); Shuo Shan, Shenzhen (CN)

(73) Assignee: LIFETECH SCIENTIFIC (SHENZHEN) CO., LTD., Shenzhen (CN)

( * ) Notice: Subject to any disclaimer, the term of this patent is extended or adjusted under 35 U.S.C. 154(b) by 0 days.

(21) Appl. No.: 17/779,694

(22) PCT Filed: Dec. 15, 2020

(86) PCT No.: PCT/CN2020/136418
§ 371 (c)(1),
(2) Date: May 25, 2022

(87) PCT Pub. No.: WO2021/129455
PCT Pub. Date: Jul. 1, 2021

(65) Prior Publication Data
US 2022/0409255 A1  Dec. 29, 2022

(30) Foreign Application Priority Data
Dec. 27, 2019  (CN) .......................... 201911376599.8
Dec. 27, 2019  (CN) .......................... 201911379612.5

(51) Int. Cl.
*A61B 18/02*  (2006.01)
*A61B 17/12*  (2006.01)
*A61B 18/00*  (2006.01)

(52) U.S. Cl.
CPC ........ *A61B 18/02* (2013.01); *A61B 17/12122* (2013.01); *A61B 17/12172* (2013.01);
(Continued)

(58) Field of Classification Search
CPC .......... A61B 18/02; A61B 2018/00357; A61B 2018/00577; A61B 2018/0063; A61B 2018/0212; A61B 2018/0287
See application file for complete search history.

(56) References Cited

U.S. PATENT DOCUMENTS 6,106,518 A * 8/2000 Wittenberger ......... A61B 18/02
606/23
2002/0068928 A1* 6/2002 Werneth ................ A61B 18/02
606/21
(Continued)

FOREIGN PATENT DOCUMENTS

CN  207785227 U  8/2018
CN  208002885 U  10/2018
(Continued)

OTHER PUBLICATIONS

International Search Report dated Mar. 12, 2021, in corresponding to International Application No. PCT/CN2020/136418; 8 pages (with English Translation).
(Continued)

*Primary Examiner* — Daniel W Fowler
(74) *Attorney, Agent, or Firm* — Maier & Maier, PLLC (57) ABSTRACT

A left atrial appendage (LAA) occluder and an occluding system are provided. The LAA occluder includes a sealing portion and an ablation portion arranged in the sealing portion, as well as a hollow proximal connector at a proximal end of the sealing portion. The ablation portion is connected to the proximal connector. The ablation portion is
(Continued)

used to freeze an LAA after being injected with cryogen so as to form an annular isolation band on an inner wall of the LAA for blocking the conduction of electrical signals between the LAA and a left atrium.

13 Claims, 7 Drawing Sheets

(52) U.S. Cl.
CPC ............. *A61B 2018/00357* (2013.01); *A61B 2018/00577* (2013.01); *A61B 2018/0063* (2013.01); *A61B 2018/0212* (2013.01); *A61B 2018/0287* (2013.01)

(56) References Cited

U.S. PATENT DOCUMENTS

| | | | | |
|---|---|---|---|---|
| 2005/0273095 | A1* | 12/2005 | Taimisto | A61B 18/1492 606/41 |
| 2006/0069385 | A1* | 3/2006 | Lafontaine | A61B 18/02 606/23 |
| 2006/0212027 | A1* | 9/2006 | Marrouche | A61B 18/02 606/23 |
| 2009/0177262 | A1 | 7/2009 | Oberti et al. | |
| 2011/0190751 | A1* | 8/2011 | Ingle | A61B 18/02 606/21 |
| 2015/0094700 | A1* | 4/2015 | Iwata | A61B 18/02 606/20 |
| 2016/0135864 | A1* | 5/2016 | Babkin | A61B 18/02 606/25 |
| 2016/0143522 | A1* | 5/2016 | Ransbury | A61B 5/0071 600/116 |
| 2017/0164999 | A1* | 6/2017 | Hettel | A61B 18/1492 |
| 2021/0282830 | A1* | 9/2021 | Xiao | A61B 18/02 |

FOREIGN PATENT DOCUMENTS

| | | |
|---|---|---|
| CN | 109124755 A | 1/2019 |
| CN | 109419548 A | 3/2019 |
| CN | 109475378 A | 3/2019 |
| CN | 110115608 A | 8/2019 |
| CN | 209203496 U | 8/2019 |
| CN | 110573093 A | 12/2019 |
| WO | 2018058033 A1 | 3/2018 |

OTHER PUBLICATIONS

First Office Action dated Oct. 11, 2021, corresponding to Chinese Application No. 201911379612.5; 10 pages (with English Translation).
First Search dated Sep. 29, 2021, corresponding to to Chinese Application No. 201911379612.5; 1 page.
First Office Action dated Oct. 11, 2021, corresponding to Chinese Application No. 201911376599.8; 14 pages (with English Translation).
First Search dated Sep. 28, 2021, corresponding to Chinese Application No. 201911376599.8; 1 page.
Notification to Grant Patent Right for Invention dated Apr. 2, 2022 in corresponding Chinese Application No. 201911379612.5; 13 pages.
Notification to Grant Patent Right for Invention dated Apr. 7, 2022 in corresponding Chinese Application No. 201911376599.8; 32 pages.
Examination Report dated Nov. 16, 2022, in corresponding Indian Application No. 202217032502, 6 pages.

* cited by examiner

LEFT ATRIAL APPENDAGE OCCLUDER AND OCCLUSION SYSTEM

TECHNICAL FIELD

The embodiments relate to the field of interventional medical instruments, particularly to a left atrial appendage (LAA) occluder and an occluding system.

BACKGROUND

Atrial fibrillation is the most common arrhythmia in clinical practice, with an incidence of 1.0%-1.5%, which increases with age. Atrial fibrillation may impair the cardiac function of patients and induce thrombosis, seriously affecting the quality of life. Atrial fibrillation is the strongest risk factor for stroke and heart failure, and 20% of stroke events are related to atrial fibrillation, which causes a great threat to the life safety of patients.

Atrial fibrillation is mainly caused by the disorder of electrical signals in heart. The special structures of pulmonary vein (vena cava) muscle sleeve and atria such as ridge, venous sinus and Marshall ligament may generate electrical activities spontaneously, which may drive or trigger an atrial electrical activity to cause atrial fibrillation accordingly. In 1997, Haissaguerre found that the electrical activity of the pulmonary vein muscle sleeve could drive/trigger the atrial electrical activity to cause atrial fibrillation and therefore proposed that isolation of an electrical connection between a pulmonary vein and a left atrium by radiofrequency catheter ablation could terminate atrial fibrillation. Transcatheter ablation of atrial fibrillation has gone through the difficult exploration process of optimizing the surgical method. So far, it has been agreed that circumferential pulmonary vein ablation is the surgical cornerstone and the necessary ablation diameter can be increased as needed and the fragmentation potential and nerve plexus ablation can also be increased on this basis. However, conventional ablation usually has the disadvantages of long operation time, large ablation area and incomplete ablation, and cannot completely prevent current foldback, resulting in the possibility of recurrence of atrial fibrillation.

Left atrial appendage (LAA) is not only the main part of thrombosis caused by atrial fibrillation (AF), but also one of the key regions for its occurrence and maintenance due to the special morphology and structure thereof. Some patients with atrial fibrillation can benefit from an active left atrial appendage isolation (LAAI). In addition, aggressive ablation in the left atrium is often required for non-paroxysmal atrial fibrillation to reach an ablation endpoint, which is prone to a passive LAAI. An iatrogenic LAAI associated with ablation can theoretically increase the risk of thromboembolic events, which requires a high degree of vigilance by electrophysiologists.

Catheter ablation around pulmonary veins is generally accepted as a treatment for atrial fibrillation, but it is difficult to perform catheter ablation, the operation time is long, and it is easy to cause recurrence of atrial fibrillation. A passive LAAI leads to cerebrovascular embolism and other diseases, and patients often need to re-ablation or long-term oral anticoagulant to avoid such diseases. A left atrium electrical isolation has a good effect on long-term maintenance of sinus rhythm, but the left atrial electrical isolation is prone to thrombosis in the LAA, leading to cerebrovascular embolism events.

SUMMARY

Based on this, the embodiments provide an LAA occluder and an occluding system to solve the problems of high operational difficulty and high risk in implementing an active LAAI.

An LAA occluder is proposed, including a sealing portion. The sealing portion includes an ablation portion arranged in the sealing portion, and a hollow proximal connector arranged at a proximal end of the sealing portion. The ablation portion is connected to the proximal connector. The ablation portion is configured to freeze an LAA after being injected with cryogen so as to form an annular isolation band on an inner wall of the LAA. The annular isolation band is configured to block the conduction of electrical signals between the LAA and a left atrium. When the sealing portion is in a compressed state, the ablation portion is folded and accommodated in the sealing portion, and the ablation portion abuts against at least a circumferential edge of the sealing portion after being unfolded in the sealing portion.

An occluding system is also proposed, including the above-described LAA occluder, and further including a pushing tube, a delivery sheath and a catheter portion. The pushing tube is movably arranged in the delivery sheath and detachably connected to the proximal connector of the sealing portion. The catheter portion is movably arranged in the pushing tube and detachably connected to the proximal connector.

The embodiments provide an LAA occluder and an occluding system. An ablation member connected to a proximal connector is arranged in a sealing portion of the LAA occluder, and the ablation member is delivered to an LAA together with the LAA occluder. While the LAA occluder occludes an ostium of the LAA, the ablation member freezes the LAA after being injected with cryogen so as to form an annular isolation band on an inner wall of the LAA, thereby blocking the conduction of electrical signals between the LAA and a left atrium, achieving electrical isolation between the LAA and the left atrium, enabling a patient to enjoy the benefits of long-term maintenance of sinus rhythm after the electrical isolation between the LAA and the left atrium, reducing the probability of thrombus formation at the LAA, reducing the operational difficulty and risk of an active LAAI, and also achieving the occlusion of the LAA. Under the dual effects of the electrical isolation and the occlusion, the occurrence of stroke can be better prevented, and the postoperative treatment effect is better.

Another occluding system is also proposed, including an LAA occluder, a pushing tube, a delivery sheath, and an ablation member. The LAA occluder includes a sealing portion that is internally hollow and has an opening at a proximal end. The pushing tube is movably arranged in the delivery sheath and detachably connected to the proximal end of the sealing portion. The ablation member is accommodated with the LAA occluder in the delivery sheath in a delivery state. An ablation portion is accommodated in the sealing portion. After the LAA occluder is unfolded in an LAA, the ablation portion is configured to freeze the LAA after being injected with cryogen so as to form an annular isolation band on an inner wall of the LAA. The annular isolation band is configured to block the conduction of electrical signals between the LAA and a left atrium. According to the occluding system, an ablation member delivered to the LAA together with an LAA occluder is used. While the LAA occluder occludes an ostium of the LAA, the ablation member freezes the LAA in cooperation with cryogen so as to form an annular isolation band on an inner wall of the LAA, thereby blocking the conduction of electrical signals between the LAA and the left atrium, achieving electrical isolation between the LAA and the left atrium, enabling a patient to enjoy the benefits of long-term maintenance of sinus rhythm after the electrical isolation between the LAA and the left atrium, reducing the probability of thrombus formation at the LAA, reducing the operational difficulty and risk of an active LAAI, and also achieving the occlusion of the LAA. Under the dual effects of the electrical isolation and the occlusion, the occurrence of stroke can be better prevented, and the postoperative treatment effect is better.

DETAILED DESCRIPTION OF THE EMBODIMENTS

In order to facilitate the understanding of the embodiments, the embodiments will be described more comprehensively below with reference to relevant drawings. Various implementations of the embodiments are given in the drawings. However, the embodiments may be implemented in many different forms, and are not limited to the implementations described herein. Conversely, these implementations are provided so that the embodiments herein are understood more thoroughly and comprehensively.

It should be noted that when an element is referred to as being "fixed" or "arranged" to another element, it may be directly on another element or centered elements may also be present. When an element is referred to as being "connected" to another element, it may be directly connected to another element or centered elements may also be present. The terms "vertical", "horizontal", "left", "right" and the like as used herein are for illustrative purposes only and are not meant to be the only implementations.

Unless defined otherwise, all technical and scientific terms used herein have the same meaning as commonly understood by those skilled in the art to which the disclosure belongs. The terms used herein are for the purpose of describing implementations only and are not intended to be limiting. The term "and/or" as used herein includes any and all combinations of one or more of the associated listed items.

In the field of interventional medical instruments, an end of a medical instrument implanted in a human or animal body that is closer to an operator is generally referred to as a "proximal end", an end that is further away from the operator is referred to as a "distal end", and the "proximal end" and "distal end" of any component of the medical instrument are defined in accordance with this principle. A position where a left atrium enters an LAA is defined as an ostium of the LAA and a position in the LAA adjacent to an entrance to the LAA is defined as a neck of the LAA. An "axial direction" generally refers to a longitudinal direction of the medical instrument when being delivered, and a "radial direction" generally refers to a direction of the medical instrument perpendicular to the "axial direction" thereof, and the "axial direction" and "radial direction" of any component of the medical instrument are defined in accordance with this principle.

Figure 1:
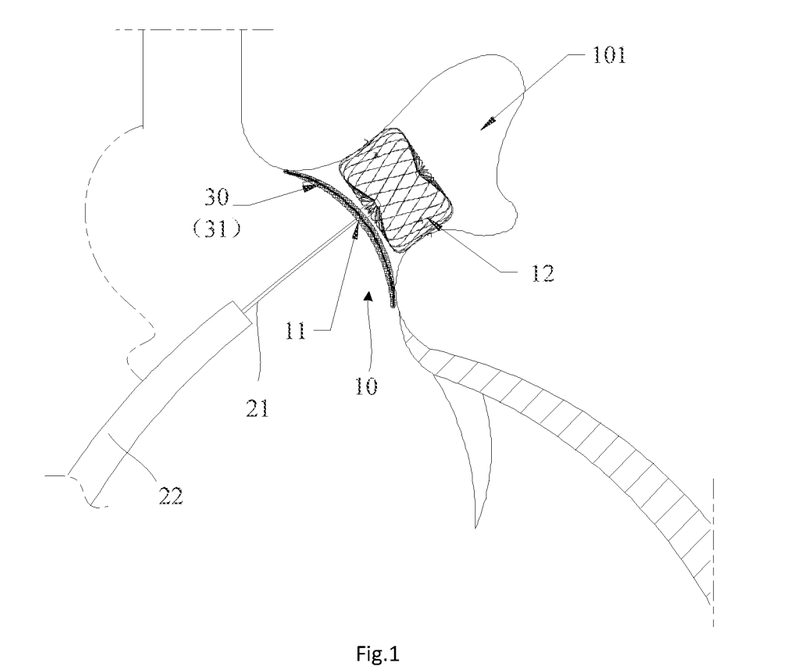
FIG. 1 is a schematic view of an LAA occluder implanted at an LAA position in an occluding system according to an embodiment.

FIG. 1 shows a schematic view of an occluding system according to the disclosure after an LAA occluder 10 is implanted into an LAA 101. Referring to FIG. 1, the occluding system includes the LAA occluder 10, a freezing device, a pushing tube 21, a delivery sheath 22, and an ablation member 30 having an ablation portion 31.

The LAA occluder 10 includes a sealing portion 11 and a fixing portion 12 connected to the sealing portion 11. The sealing portion 11 and the fixing portion 12 may be connected directly or through an intermediate member. The sealing portion 11 may have a disc-like, columnar or plug-like structure, which is not limited herein. The sealing portion 11 is internally hollow and has an opening at a proximal end so that the ablation portion 31 of the ablation member 30 is inserted into a sealing disc 10 from the opening. The shape of the fixing portion 12 is not limited and may be a column shape or an umbrella shape.

With continued reference to FIG. 1, the pushing tube 21 is movably arranged in the delivery sheath 22 and detachably connected to the proximal end of the sealing portion 11 so that the LAA occluder 10 can be released from a distal end of the delivery sheath 22 by manipulating the relative movement between the pushing tube 21 and the delivery sheath 22. For example, in some implementations, when the LAA occluder 10 is pushed to the vicinity of the LAA 101 under the delivery of the pushing tube 21 and the delivery sheath 22, the delivery sheath 22 is withdrawn proximally relative to the pushing tube 21 so that the LAA occluder 10 connected to a distal end of the pushing tube 21 is exposed from a distal end of the delivery sheath 22 and is self-expanded and released.

It should be noted that when the LAA occluder 10 is implanted into the LAA 101, the fixing portion 12 is located in a cavity of the LAA 101 and closely attached to a cavity wall of the LAA 101 to prevent the LAA occluder 10 from falling out of the LAA 101. The sealing portion 11 occludes the ostium of the LAA 101, prevents thrombus formed in the cavity of the LAA from flowing into a left atrium, and prevents blood flow from the left atrium into the cavity of the LAA 101.

In the occluding system provided by the disclosure, the freezing device is connected to the ablation member 30 for providing cryogen to the ablation portion 31 of the ablation member 30. In a delivery state, the ablation member 30 is accommodated with the LAA occluder 10 in the delivery sheath 21, and the ablation portion 31 is accommodated in the sealing portion 11, so that the ablation member 30 can be delivered to the LAA 101 together with the LAA occluder 10. After the LAA occluder 10 is unfolded in the LAA 101, the ablation portion 31 located in the sealing portion 11 freezes the LAA in cooperation with cryogen so as to form an annular isolation band on the inner wall of the LAA 101. The annular isolation band is configured to block the conduction of electrical signals between the LAA 101 and the left atrium, thereby achieving electrical isolation between the LAA 101 and the left atrium, achieving the effect of electrical isolation, and enabling a patient to enjoy the benefits of long-term maintenance of sinus rhythm after the electrical isolation of the LAA 101.

In addition, in such a manner that occlusion and ablation are achieved by the ablation member 30 being delivered to the LAA 101 together with the LAA occluder 10, that is, after the LAA occluder 10 is released in the LAA 101, the sealing portion 11 occludes the ostium of the LAA 101. Since the ablation portion 31 of the ablation member 30 is located in the sealing portion 11, the ablation portion 31 will perform cryoablation on the inner wall of the LAA 101 in cooperation with the cryogen injected therein. And the ablation portion 31 circumferentially abuts against the inner wall of the LAA 101 to be annular or nearly annular after being unfolded, thereby forming an annular isolation band on the inner wall of the LAA 101 under the action of cryogen. Therefore, the occluding system of the disclosure can occlude the LAA 101 by using the LAA occluder 10 while annularly freezing the inner wall of the LAA 101 by inflating the ablation portion 31 with cryogen, so as to achieve the electrical isolation between the LAA 101 and the left atrium and the dual assurance of occlusion and ablation, thereby further preventing a patient from having a stroke.

Figure 2:
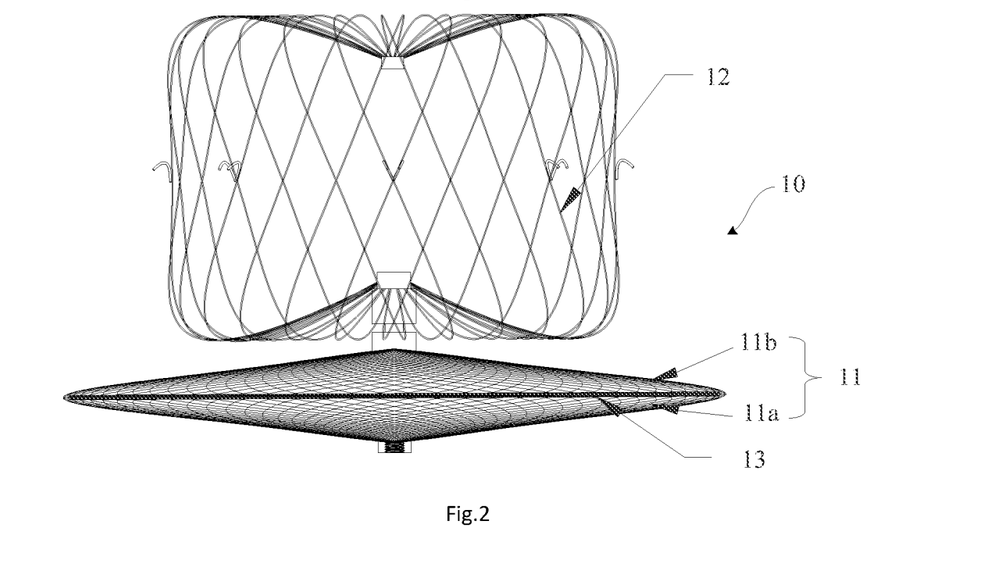
FIG. 2 is a structural schematic view of an LAA occluder of an occluding system according to an embodiment.

For convenience in further describing the structure of the LAA occluder 10 as shown in FIG. 2, taking a disc-shaped sealing portion 11 as an example, the surface of a side where the proximal end of the sealing portion 11 is located is referred to as a "proximal disc surface 11a", and accordingly, the surface of a side where the distal end of the sealing portion 11 is located is referred to as a "distal disc surface 11b". At least one flow blocking membrane (not shown) is arranged inside or outside the fixing portion 12, so as to achieve multiple occlusions in cooperation with the sealing portion 11 and improve the occlusion performance of the LAA 101. At least one flow blocking membrane is arranged on the sealing portion 11. For example, the proximal disc surface 11a and/or the distal disc surface 11b are covered with a flow blocking membrane. As shown in FIG. 2, at least one flow blocking membrane 13 is arranged inside the sealing portion 11 for preventing the circulation of blood from the left atrium into the LAA 101, so as to ensure that the ostium of the LAA 101 is tightly occluded.

In this embodiment, when the ablation portion 31 of the ablation member 30 is inserted into the sealing portion 11, the flow blocking membrane 13 is located on a side where the distal end of the ablation portion 31 is located, so as to ensure that the occlusion effect of the flow blocking membrane 13 is not disturbed by the ablation member 30. For example, the flow blocking membrane 13 of the sealing portion 11 is arranged between the proximal disc surface 11a and the distal disc surface 11b, and the flow blocking membrane 13 is located between the ablation portion 31 and the distal disc surface 11b, so that a good occlusion effect of the flow blocking membrane 13 can be maintained while achieving ablation.

The size of the flow blocking membrane 13 on the sealing portion 11 is equivalent to the size of a disc surface of the sealing portion 11, so that the flow blocking membrane 13 can completely cover the disc surface of the sealing portion 11 to achieve tight occlusion. For example, when the flow blocking membrane 13 and the sealing portion 11 are both regularly circular, the diameter of the flow blocking membrane 13 is equal to or less different from the diameter of the sealing portion 11. The flow blocking membrane 13 is a polymer material, preferably polytetrafluoroethylene (PTFE) or polyethylene terephthalate (PET).

In some embodiments, the sealing portion 11 is formed into a disc-shaped structure by heat treatment using a woven mesh tube structure. An edge of the flow blocking membrane 13 is fixed onto a woven wire of the sealing portion 11 by means of suturing or bonding, and the manner of fixing the flow blocking membrane 13 to the sealing portion 11 is not limited herein.

It should be noted that most of LAA occluders 10 adopt the structures of filling in the LAA 101 and sealing the ostium of the LAA 101, including a plug structure form and a double-disc structure.

In the occluding system in the embodiments, the LAA occluder 10 includes both split and integrally formed structures. It may be appreciated that a portion of the integrally formed LAA occluder 10 for occlusion may be regarded as the sealing portion 11 in the embodiments, and a portion thereof for fixing the LAA occluder 10 may be regarded as the fixing portion 12 in the embodiments. The sealing portion 11 and the fixing portion 12 in the LAA occluder 10 may also be integrally provided. For example, the whole LAA occluder 10 is cylindrical, a portion of the proximal disc surface thereof for occlusion is equivalent to the sealing portion 11 in the disclosure, and a side wall portion thereof is configured to fix the LAA occluder 10 in the cavity of the LAA, thus being equivalent to the fixing portion 12 in the embodiments.

Embodiments will now be further described by taking a split-type double-disc structure of the LAA occluder 10 as an example.

Embodiment 1

Figure 3:
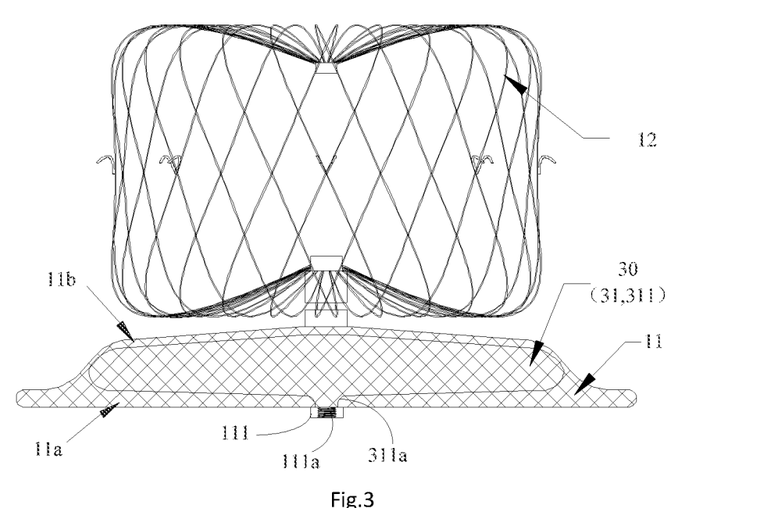
FIG. 3 is a schematic view of an LAA occluder of an occluding system of Embodiment 1 combined with a balloon.

As shown in FIG. 3, the ablation portion 31 of the ablation member 30 is a balloon 311 having an open end 311a. The balloon 311 is arranged in the sealing portion 11. For example, in an embodiment where the sealing portion 11 includes a proximal disc surface 11a and a distal disc surface 11b, the balloon 311 is located between the proximal disc surface 11a and the distal disc surface 11b of the sealing portion 11.

The open end 311a of the balloon 311 is sleeved on the proximal end of the sealing portion 11, and connected with a proximal end opening of the sealing portion 11. The proximal end opening of the sealing portion 11 may be a through hole structure provided at the proximal end of the sealing portion 11 or may be a tube arranged at the proximal end of the sealing portion 11 and connected with the interior of the sealing portion 11. The structure and shape of the proximal end opening of the sealing portion 11 are not limited herein, and it is only sufficient to enable cryogen to be injected into the balloon 311 by means of a catheter.

For example, in some embodiments, as shown in FIG. 3, the proximal end of the sealing portion 11 is provided with a proximal connector 111. The proximal connector 111 is in the shape of a hollow tube. Specifically, the proximal connector 111 has a tube hole 111a so that the tube hole 111a of the proximal connector 111 constitutes the proximal opening of the sealing portion 11.

In this embodiment, the open end 311a of the balloon 311 is sleeved on the proximal connector 111, and the open end 311a of the balloon 311 is connected with a cavity of the proximal connector 111. Thus, the interior of the balloon 311 is connected with the tube hole 111a of the proximal connector 111, so that the balloon 311 may be inflated with cryogen such as $N_2O$ from the tube hole 111a. The connection and fixing mode between the balloon 311 and the proximal connector 111 is not limited, such as glue bonding or clamp connection. Using cryogen injected into the balloon 311, the inflated balloon 311 abuts, at least circumferentially, against the inner wall of the LAA 101, so as to form an annular freezing region at the neck or ostium of the LAA 101. After myocardial tissues at the freezing region are damaged by freezing, an annular isolation band is formed on the inner wall of the LAA 101, so as to use the annular isolation band to block the conduction of electrical signals between the LAA 101 and the left atrium, thereby achieving cryoablation.

With this structural arrangement, when the LAA 101 is occluded by the LAA occluder 10, the ablation may be achieved by injecting cryogen through the balloon 311 arranged therein, so that the occlusion and ablation of the LAA 101 can be completed in one operation, thereby reducing the difficulty of operation, shortening the operation time, reducing the cost, and greatly reducing the probability of stroke of the patient. In addition, since the electrical isolation between the LAA 101 and the left atrium can be achieved while the LAA 101 is occluded, a patient can maintain sinus rhythm for a long time without the risk of cerebrovascular blockage or the like due to the fall-out of thrombus in the LAA 101.

The balloon 311 may be made of a compliant material, such as a polyamide and polyether block copolymer. Polyamides are aliphatic, such as nylon 12, nylon 11, nylon 9, nylon 6, nylon 6/12, nylon 6/11, nylon 6/9, and nylon 6/6. Polyether blocks may be selected from polyoxytetramethylene glycol, tetramethylene ether, polyethylene glycol or polypropylene glycol. Due to the good compliance of the balloon 311, the accommodation of the balloon 311 in the sealing portion 11 during delivery does not affect the size selection of the delivery sheath 22, and the balloon 311 can be rapidly expanded after being injected with cryogen, and can sufficiently abut against the circumferential edge of the sealing portion 11 when being inflated to a certain extent, so that an annular isolation band can be formed on the inner wall of the LAA 101 by means of the cryogen, thereby achieving the electrical isolation between the LAA 101 and the left atrium.

Thus, the shape of the balloon 311 may be changed accordingly according to the degree of inflation of the balloon 311, so as to match the traction of the fixing portion 12 on the sealing portion 11 and enhance the fitting degree between the sealing portion 11 and the ostium of the LAA 101, thereby improving the stability and occlusion performance of the LAA occluder 10.

In an embodiment where the flow blocking membrane 13 is arranged in the sealing portion 11, the flow blocking membrane 13 of the sealing portion 11 may be arranged between the proximal disc surface 11a and the distal disc surface 11b, and the flow blocking membrane 13 is located between the balloon 311 and the distal disc surface 11b, namely, the balloon 311 is located on a side where the proximal end of the flow blocking membrane 13 is located, so as to ensure that the occlusion effect of the flow blocking membrane 13 is not disturbed by the balloon 311.

Figure 4A:
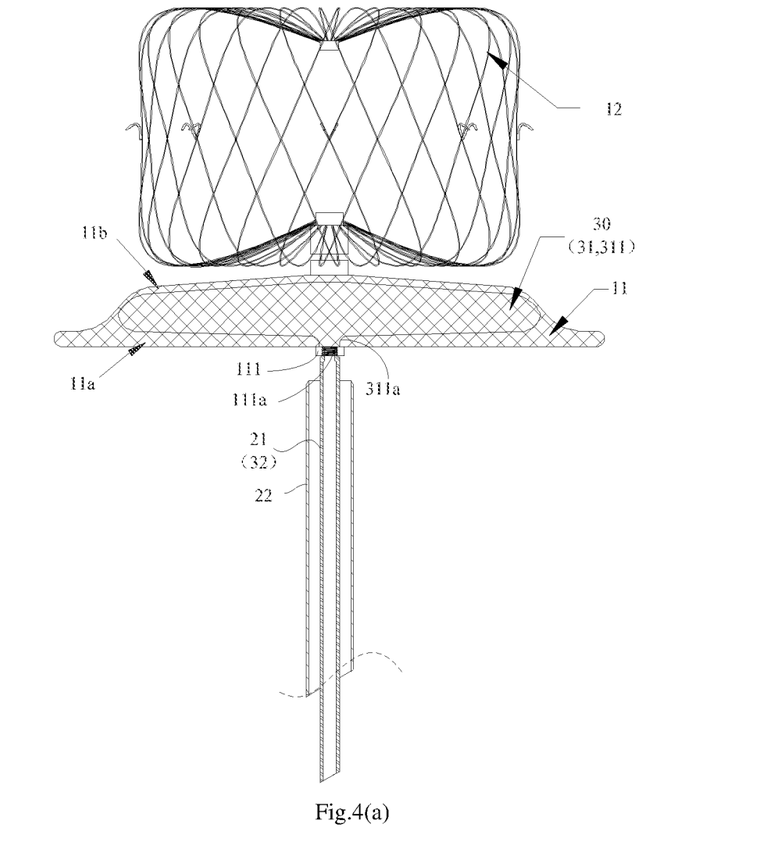
FIG. 4(a) is a partial structural schematic view of one implementation of the occluding system of Embodiment 1.

Referring to FIGS. 1 and 4(a), in the occluding system provided by the embodiments, the ablation member 30 further includes a catheter portion 32 connected directly or indirectly to the ablation portion 31, and a proximal end of the catheter portion 32 is connected to the freezing device for delivering cryogen to the balloon 311. The sealing portion 11 is in a compressed state when being accommodated in the delivery sheath 22, and the ablation portion 31 (i.e., the balloon 311) is folded and accommodated in the sealing portion 11. The balloon 311, after being unfolded in the sealing portion 11, abuts at least against the circumferential edge of the sealing portion 11 to better perform cryoablation on the LAA 101.

It should be noted that the catheter portion 32 may be formed by a pushing tube 21 that is internally hollow or may be formed by a tube independent of the pushing tube 21. The structure of the occluding system will be further described below for each of these two cases respectively.

In some embodiments, the pushing tube 21 is connected to the proximal end of the sealing portion 11 to not only push the LAA occluder 10 into the LAA 101, but meanwhile, a cavity of the pushing tube 21 is connected with the proximal end opening of the sealing portion 11 for injecting cryogen into the balloon 311 located in the sealing portion 11 through the pushing tube 21. Further, an embolic agent may be injected into the balloon 311 after cryoablation through the pushing tube 21, so as to realize multiple occlusions after inflating the balloon 311, so as to improve the sealing performance of the sealing portion 11.

With reference to FIG. 4(a), in an embodiment where the proximal end of the sealing portion 11 is provided with the proximal connector 111, the distal end of the pushing tube 21 is detachably connected to the proximal connector 111, so that the cavity of the pushing tube 21 is communicated with the tube hole 111a of the proximal connector 111. Thus, the pushing tube 21 can not only be used for pushing the LAA occluder 10 to satisfy the delivery requirements of the LAA occluder 10 and the balloon 311, and the pushing tube 21 can also serve as the catheter portion 32 of the ablation member 30 to satisfy the injection of cryogen into the balloon 311 to freeze the LAA 101.

In this embodiment, after the pushing tube 21 is connected to the proximal connector 111, the LAA occluder 10 is accommodated together with the pushing tube 21 in the delivery sheath 22 and delivered to the LAA 101 in a body. After the LAA occluder 10 is released in the LAA 101, the proximal connector 111 and the pushing tube 21 are not disconnected first. Under the situation that the proximal end of the pushing tube 21 is connected to the freezing device, cryogen delivered via the pushing tube 21 may be injected into the balloon 311 using the tube hole 111a of the proximal connector 111, so that the cooperation of the proximal connector 111 and the pushing tube 21 can not only meet the need for delivery of the LAA occluder 10, but also meet the need for injecting cryogen into the balloon 311 for cryoablation, reduce the number of tubes required for delivery of the LAA occluder 10, and meet the demand for a small overall tube diameter of an assembly for delivery. After cryoablation, the proximal connector 111 is disconnected from the pushing tube 21, and the pushing tube 21 and the delivery sheath 22 are withdrawn from the body.

There are several possible structures for the connection of the pushing tube 21 to the proximal connector 111. For example, in some embodiments, the tube hole 111a of the proximal connector 111 may be a threaded hole, and the distal end of the pushing tube 21 is in threaded fit with the tube hole 111a of the proximal connector 111. In other embodiments, the distal end of the pushing tube 21 is connected to the proximal connector 111 through a buckle. In other implementations, the pushing tube 21 may be connected to the proximal connector 111 by other means, so long as they are connected, for example to provide communication with the interior of the balloon 311 through a cavity of the pushing tube 21 to meet the need to inject cryogen into the balloon 311.

In other embodiments, the occluding system may include two internally hollow catheters. One of the catheters is the pushing tube 21. The distal end of the catheter is detachably connected to the proximal connector 111 for pushing the LAA occluder 10. The other catheter is configured to inflate the balloon 311 with cryogen to achieve cryoablation of the LAA 101.

Figure 4B:
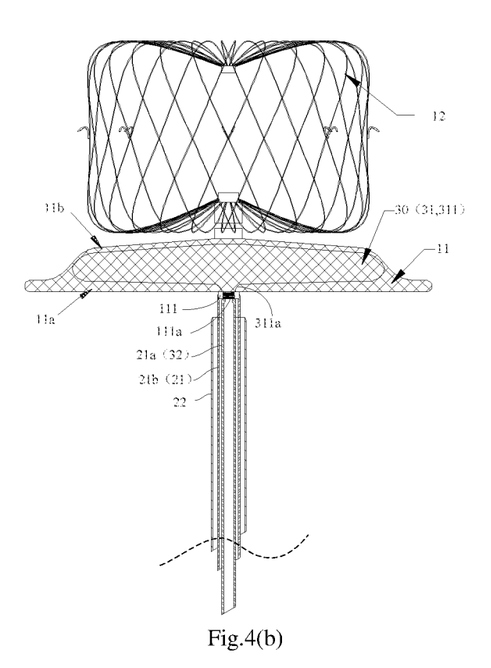
FIG. 4(b) is a partial structural schematic view of another implementation of the occluding system of Embodiment 1.

For convenience of description, one of the catheters is referred to as a first catheter 21a and the other catheter is referred to as a second catheter 21b. The "second catheter 21b is also the pushing tube 21. In some embodiments, the first catheter 21a is sleeved inside the second catheter 21b, and they are axially movable relative to each other. In other embodiments, the first catheter 21a and the second catheter 21b are not sleeved together, and the first catheter 21a and the second catheter 21b may have the same or different diameters.

Specifically, as shown in FIG. 4(b), the ablation member 30 further includes a catheter portion 32. The catheter portion 32 includes a first catheter 21a. The first catheter 21a is an internally hollow tubular body. The outer diameter of the first catheter 21a is smaller than the inner diameter of the second catheter 21b. The first catheter 21a is sheathed inside the second catheter 21b, and the first catheter 21a is axially movable in a cavity of the second catheter 21b. A distal end of the second catheter 21b is detachably connected to the proximal connector 111, a distal end of the first catheter 21a extends into the proximal connector 111, and a cavity of the first catheter 21a is connected with the tube hole 111a of the proximal connector 111. The distal end of the first catheter 21a may abut in the proximal connector 111 or may be detachably connected to the proximal connector 111. For example, the distal end of the second catheter 21b may be detachably connected to the proximal connector 111 through an external thread provided on the outer wall of the proximal connector 111, and the distal end of the first catheter 21a may be detachably connected to the proximal connector 111 through an internal thread provided on the inner wall of the proximal connector 111. During delivery, both the first catheter 21a and the second catheter 21b are delivered to the LAA 101 together with the LAA occluder 10. After the LAA occluder 10 is released, cryoablation is performed by injecting cryogen into the balloon 311 in the sealing portion 11 through the first catheter 21a. After cryoablation, the proximal connector 111 is disconnected from the first catheter 21a and the second catheter 21b, and the first catheter 21a, the second catheter 21b and the delivery sheath 22 are withdrawn from the body.

In other embodiments, only the second catheter 21b is connected to the proximal connector 111 and delivered to the LAA 101 along with the LAA occluder 10 during the delivery of the LAA occluder 10. When it is required to perform cryoablation on the LAA 101 after the LAA occluder 10 is unfolded at the LAA 101, the first catheter 21a may be pushed along the cavity of the second catheter 21b, and then the first catheter 21a may be connected to the proximal connector 111, so that the cavity of the first catheter 21a is connected with the interior of the balloon 311, and then the cryogen may be injected into the balloon 311 through the first catheter 21a to achieve cryoablation on the LAA 101. The cryoablation is simple in operation and high in safety. After the ablation is completed, the first catheter 21a and the second catheter 21b may be disconnected from the proximal connector 111 after the cryogen is withdrawn from the body, and the first catheter 21a and the second catheter 21b may be withdrawn from the body together with the delivery sheath 22.

It should be noted that the manner in which the first catheter 21a and the second catheter 21b are used in cooperation for the delivery and cryoablation of the LAA occluder 10 is not limited to the above-described exemplary case. For example, in other implementations, after the LAA occluder 10 is unfolded at the LAA 101, cryoablation is performed on the LAA 101 by injecting cryogen into the balloon 311 through the first catheter 21a. Then, the first catheter 21a is withdrawn again, and the embolic agent is delivered into the balloon 311 through the second catheter 21b, so as to fill the interior of the sealing portion 11 after the balloon 311 is inflated, thereby achieving the re-occlusion of the neck or ostium of the LAA 101. Multiple occlusions can improve the sealing performance of the sealing portion 11. In other embodiments, the pushing tube 21 is another hollow tube than the second tube 21b described above, and the catheter portion 32 includes a first catheter 21a and a second catheter 21b. In contrast to the above, the first catheter 21a is withdrawn after cryoablation is performed, and then the second catheter 21b is delivered along the cavity of the delivery sheath 22 to the LAA 101 and connected to the proximal connector 111 of the LAA occluder 10. Then, the embolic agent is injected into the balloon 311 through the second catheter 21b. The pushing tube 21 may be continuously connected to the proximal connector 111 when it is necessary to inject the embolic agent or may be withdrawn from the body together with the first catheter 21a when the first catheter 21a is withdrawn.

Further, in some embodiments, a distal end of the first catheter 21a has a tapered section (not shown), and an inner diameter of a distal end of the tapered section is smaller than an inner diameter of a proximal end of the tapered section. Thus, the distal end of the tapered section has a microporous structure, and the balloon 311 is inflated with cryogen by using micropores, so that the Joule-Thomson principle may be used, that is, when gas is injected from a higher pressure region into a lower pressure region through a narrow micropore, it will be throttled, and the temperature of most of the gas will suddenly decrease after throttling, thereby enhancing the freezing effect of the cryogen.

The manner of connection between the first catheter 21a and the proximal connector 111 and the manner of connection between the second catheter 21b and the proximal connector 111 may be a detachable connection manner such as threaded or locking connection, which is not limited herein.

Embodiment 2

Figure 5:
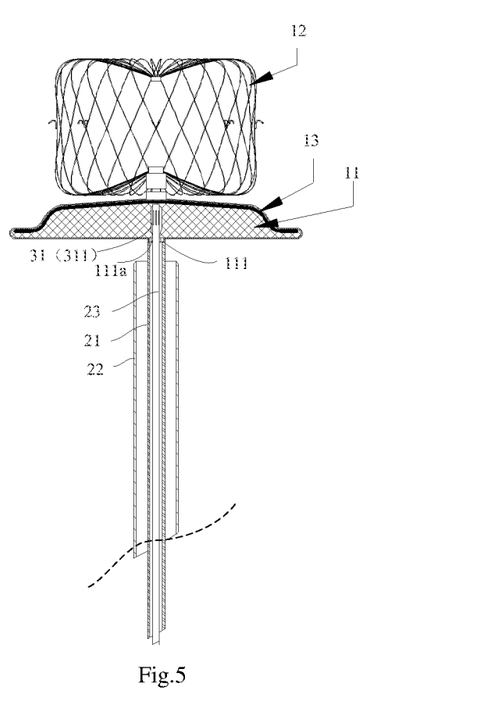
FIG. 5 is a partial structural schematic view of an occluding system of Embodiment 2, where a balloon is not inflated.
Figure 6:
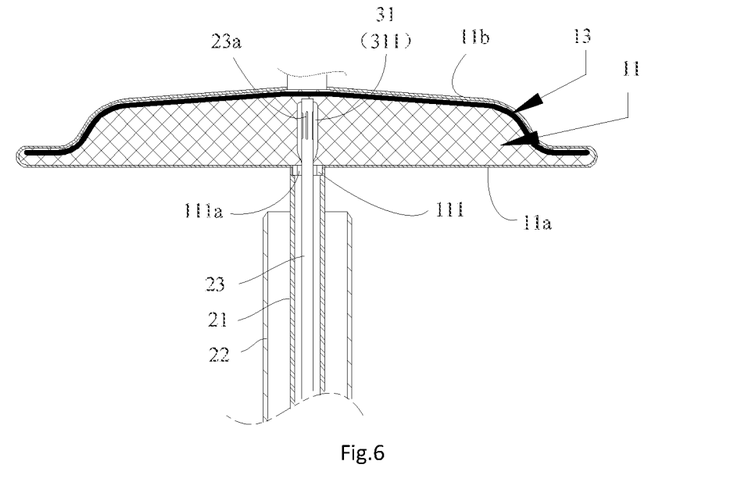
FIG. 6 is a partial structural schematic view of a sealing portion connected to an ablation member in an occluding system shown in FIG. 5.

Similar to Embodiment 1, in an occluding system of Embodiment 2, the pushing tube 21 is movably arranged in the delivery sheath 22 and can be detachably connected to the proximal end of the sealing portion 11 of the LAA occluder 10, so as to push the LAA occluder 10 into a distal tube section of the delivery sheath 22 or push out from the distal end of the delivery sheath 22 to release the LAA occluder 10. The same points or similarities between Embodiment 2 and Embodiment 1 will not be described in detail herein, and the main difference therebetween is that, as shown in FIGS. 5 and 6, in the occluding system of Embodiment 2, the balloon 311 constituting the ablation portion 31 is annular, which is fixedly sleeved on the distal end of the catheter portion 23, and the interior of the balloon 311 is communicated with the interior of the catheter portion 23. The balloon 311 and the catheter portion 23 form a balloon catheter together.

In this embodiment, in a delivery state, the distal end of the catheter portion 23 passes through the proximal end opening of the sealing portion 11, so that the balloon 311, sleeved at the distal end of the catheter portion 23, is located in the sealing portion 11 of the LAA occluder 10. Therefore, after the LAA occluder 10 is unfolded in the LAA 101, the freezing device delivers cryogen into the balloon 311 through the catheter portion 23. The balloon 311 freezes the neck or ostium of the LAA 101 in cooperation with the cryogen therein, so that after myocardial tissues at a freezing region are damaged, an annular isolation band is formed, so as to use the annular isolation band to block the conduction of electrical signals between the LAA 101 and the left atrium, thereby achieving cryoablation.

The balloon catheter is arranged in the cavity of the pushing tube 21, and the distal end of the catheter portion 23 is provided with an inflation/deflation port 23a. The balloon 311 is arranged at the distal end of the catheter portion 23, and the interior of the balloon 311 is connected with the inflation/deflation port 23a. The catheter portion 23 can inject cryogen into the balloon 311 through the inflation/deflation port 23a to meet the need for cryoablation of the neck or ostium of the LAA 101.

Figure 7:
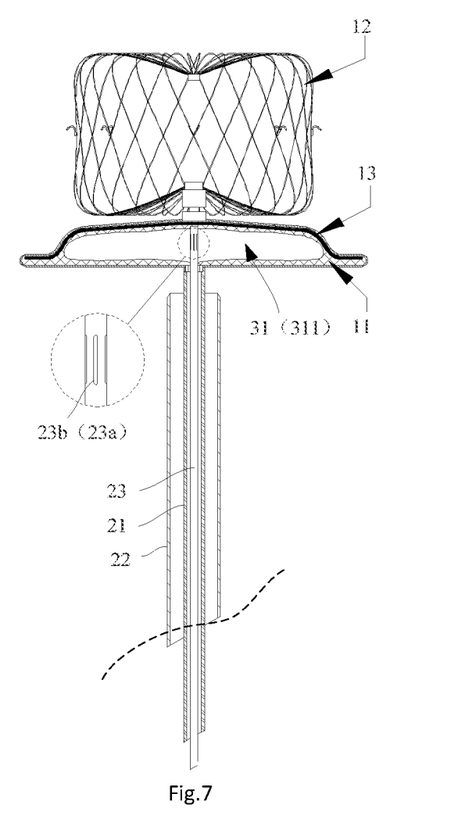
FIG. 7 is a schematic view of a balloon in an inflated state in the occluding system shown in FIG. 5.

Referring to FIG. 7, the inflation/deflation port 23a may be at least one through hole 23b formed in the sidewall of the distal end of the catheter portion 23. The balloon 311 is sleeved at a position of the catheter portion 23 where the through hole 23b is formed to communicate with the cavity of the catheter portion 23 through the through hole 23b, so that cryogen may be injected into the balloon 311 through the catheter portion 23.

In some embodiments, the inflation/deflation port 23a includes a plurality of through holes 23b, for example, two or more through holes 23b, and the plurality of through holes 23b are evenly provided along the circumferential side of the catheter portion 23, so that when the catheter portion 23 inflates the balloon 311 with cryogen through the inflation/deflation port 23a, the balloon 311 can be evenly expanded, thereby avoiding biasing to one side in the sealing portion 11 due to too quick or slow local expansion. The even inflation of the balloon 311 in the sealing portion 11 ensures that the cryogen in the balloon 311 evenly freezes the freezing region of the LAA 101 to obtain a better cryoablation effect.

The shape of the through hole 23b may be circular, square or elongated, which is not limited therein. Only when the balloon 311 is arranged at the position of the catheter portion 23 where the through hole 23b is formed, the through hole 23b can be sufficient to inflate the balloon 311 with cryogen through the cavity of the catheter portion 23.

In some implementations, after the LAA occluder 10 is connected to the distal end of the pushing tube 21, the LAA occluder 10 and the pushing tube 21 are accommodated together in the cavity of the delivery sheath 22 and delivered to the LAA 101 via the delivery sheath 22. After the LAA occluder 10 is unfolded, the balloon catheter extends from the proximal end of the pushing tube 21 into the cavity of the pushing tube 21 and delivered to the position of the LAA occluder 10 until the balloon 311 on the balloon catheter is inserted into the sealing portion 11 after passing through the tube hole 111a of the proximal connector 111. The catheter portion 23 of the balloon catheter is connected to the proximal connector 111 through threads or buckles. The proximal end of the catheter portion 23 is connected to the freezing device. After cryogen is injected into the balloon 311 through the catheter portion 23, the balloon 311 is expanded and unfolded in the sealing portion 11. The cryogen in the balloon 311 is capable of cryoablation of the neck or ostium of the LAA 101. In other implementations, the pushing tube 21 may be the balloon catheter as described above, and after the balloon catheter is connected to the proximal connector 111, the catheter portion 23 may function both to push the LAA occluder 10 and to deliver cryogen to the ablation portion 31.

In other embodiments, the balloon 311 of the non-inflated balloon catheter may be pre-inserted in the sealing portion 11 so that the balloon catheter is delivered into the LAA 101 with the aid of the pushing tube 21 and the delivery sheath 22 together with the LAA occluder 10. Cryoablation of the neck or ostium of the LAA 101 can also be achieved by injecting cryogen into the catheter portion 23 through the freezing device and delivering the cryogen into the balloon 311 via the catheter portion 23 after the sealing portion 11 is unfolded in the LAA 101.

Referring again to FIG. 6, the tube hole 111a of the proximal connector 111 on the sealing portion 11 allows the passage of the distal end of the non-inflated balloon catheter. In an example, the balloon catheter is axially movably arranged in an inner cavity of the pushing tube 21, and the distal end of the balloon catheter enables the balloon 311 to extend into the sealing portion 11 from the tube hole 111a when the balloon 311 is in a non-inflated, i.e., deflated state. With this structural arrangement, it is possible to flexibly insert the balloon 311 in the sealing portion 11 when cryoablation of the LAA 101 is required and remove the balloon 311 from the sealing portion 11 after the cryoablation operation is completed. This operation manner is convenient, safe and reliable, and provides less structural improvement to the LAA occluder 10.

The mechanism of action of the balloon catheter in cooperation with the LAA occluder 10 for cryoablation will be further described below with the example of injecting $N_2O$ into the balloon 311.

First, during implantation of the LAA occluder 10, the balloon 311 at the distal end of the balloon catheter is in a non-inflated state in which the portion of the balloon catheter where the balloon 311 is arranged is placed in the sealing portion 11 of the LAA occluder 10 and the balloon catheter is connected to the proximal connector 111 of the sealing portion 11. The balloon catheter is then delivered to the LAA 101 along with the LAA occluder 10. When the LAA occluder 10 is unfolded at the LAA 101, that is, the sealing portion 11 is self-expanded and unfolded, and occludes the ostium of the LAA 101, the balloon 311 is located between the proximal disc surface 11a and the distal disc surface 11b of the sealing portion 11.

Then, after the freezing device is connected to the proximal end of the balloon catheter, cryogen $N_2O$ is injected into the balloon 311 through the catheter portion 23. The balloon 311 will be gradually inflated by the cryogen $N_2O$ and expanded between the proximal disc surface 11a and the distal disc surface 11b of the sealing portion 11. Then, the outer wall of the balloon 311 will gradually approach an inner wall near the ostium or ostium of the LAA 101, and under the action of the cryogen $N_2O$, myocardial cells around the ostium or ostium of the LAA 101 will be necrosed due to the sudden temperature decrease, so as to form an annular isolation band. Thus, the transmission of abnormal electrical signals between the LAA 101 and the left atrium is interrupted to achieve the effect of electrical isolation between the LAA 101 and the left atrium.

Additionally, after the freezing of the cells around the ostium or neck of the LAA 101 with the cryogen $N_2O$ is completed, the cryogen $N_2O$ in the balloon 311 is withdrawn with the balloon catheter, so that the volume of the balloon 311 is reduced until the balloon 311 may be withdrawn proximally together with the catheter portion 23 to continue withdrawing proximally and eventually out of the body after passing through the proximal connector 111.

It should be noted that the balloon catheter is connected with the balloon 311 through the inflation/deflation port 23a at the distal end of the catheter portion 23. As a result, when the cryogen $N_2O$ is injected into the balloon 311 through the catheter portion 23, liquid cryogen discharged from the interior of the freezing device is sprayed into the balloon 311 through the catheter portion 23 and the inflation/deflation port 23a is rapidly gasified, and the gasified cryogen $N_2O$ rapidly inflates the balloon 311. When the liquid cryogen $N_2O$ is sprayed towards the interior of the balloon 311 and gasified, the temperature of myocardial tissues in contact with the balloon 311 rapidly decreases due to heat absorbed by surrounding tissues by the gasification of the liquid cryogen $N_2O$. For example, the temperature of the myocardial tissues stably decreases to be below $-30°$ C. In this way, since the myocardial cells in the ostium or neck of the LAA 101 are gasified and frozen by the cryogen $N_2O$, the temperature rapidly decreases (hereinafter, referred to as "freezing stage"), and after the balloon 311 is withdrawn with the catheter portion 23, the temperature of a frozen part of the ostium or neck of the LAA 101 gradually rises (hereinafter, referred to as "warming stage"). During the freezing stage, ice crystals are formed in the myocardial tissues, which lead to dehydration and necrosis of myocardial cells and destruction of cell structures. However, during the warming stage, the ice crystals melt, resulting in the blockage of microcirculation and secondary damage, and eventually irreversible damage to the myocardial tissues, thus forming an annular isolation band on the inner wall of the LAA 101, preventing the transmission of abnormal electrical signals from the LAA 101 to the left atrium, and achieving an electrical isolation effect.

Embodiment 3

Figure 8A:
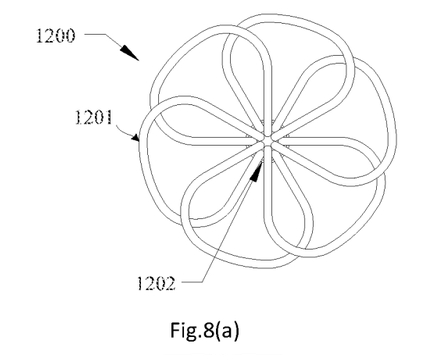
FIG. 8(a) is a schematic top view of an ablation member of an occluding system of Embodiment 3.
Figure 8B:
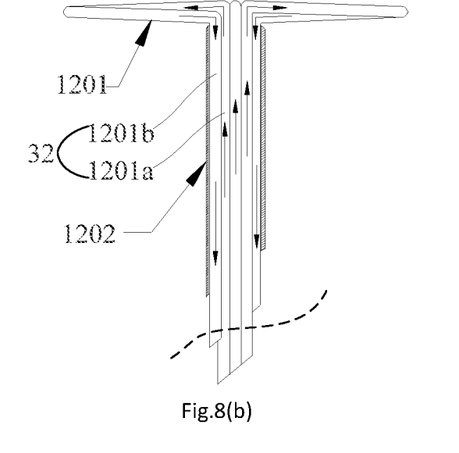
FIG. 8(b) is a schematic side view of the ablation member of the occluding system shown in FIG. 8(a)
Figure 9:
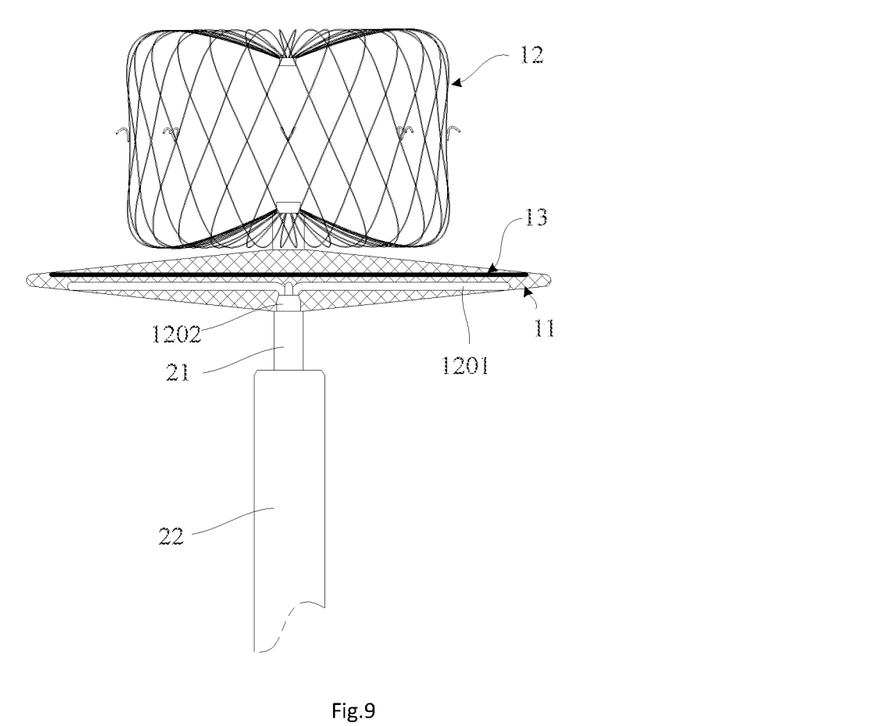
FIG. 9 is a partial structural schematic view of the occluding system of Embodiment 3.

The same points or similarities between Embodiment 3 and Embodiment 2 will not be described in detail herein, and the main difference therebetween is that the ablation portion 31 in Embodiment 2 is a balloon 311 made of high molecular material, while the ablation portion 31 in Embodiment 3 is a plurality of bent tubes made of metal. As shown in FIGS. 8(a), 8(b) and 9, the ablation member 1200 used in this embodiment is in cooperation with the LAA occluder 10 to ablate the inner wall of the LAA 101, thereby achieving electrical isolation between the LAA 101 and the left atrium. During implantation of the LAA occluder 10, the ablation portion 31 of the ablation member 1200 is folded and accommodated in the sealing portion 11, and the ablation member 1200 is delivered to the LAA 101 together with the LAA occluder 10. The ablation member 1200 includes an ablation portion 31 and a catheter portion 32, the ablation portion 31 is connected to the catheter portion 32, and the ablation portion 31 is located at the distal end of the catheter portion 32. The freezing device can deliver cryogen to the ablation portion 31 through the catheter portion 32. The ablation member 1200 and the sealing portion 11 are arranged independently of each other, and after the ablation is completed, the ablation member 1200 may be entirely withdrawn from the body.

The ablation member 1200 has some elastic deformability, i.e., can be compressed and self-expanded and unfolded, so that the ablation member 1200 can be accommodated in the delivery sheath 22 in an elongated shape. The ablation portion 31 of the ablation member 1200 may be folded and accommodated in the delivery sheath 22 so that, upon release of the ablation member 1200 from the delivery sheath 22, the ablation portion 31 of the ablation member 1200 is automatically unfolded, such as in the form shown in FIGS. 8(a) and 8(b).

The ablation member 1200 may be made of high molecular material with good resilience, and the high molecular material may be selected from one or more of a group consisting of PET, poly-L-lactide acid (PLA), poly-glycolide (PGA), poly-hydroxyalkanoate (PHA), poly-dioxanone (PDO), and poly-caprolactone (PCL).

In some embodiments, the ablation member 1200 may be made of an elastic alloy tube, such as a nitinol tube. The ablation member 1200 may be made of a high molecular tube wrapped with an elastic spring tube, and the high molecular tube may be wrapped outside the spring tube or may be embedded in the spring tube, which is not limited herein.

As shown in FIGS. 8(a) and 8(b), the ablation portion 31 of the ablation member 1200 includes a plurality of bent tubes 1201. The bent tubes 1201 fit to form a disc shape so that the ablation portion 31 is maximally radially unfolded during unfolding. Thus, the edge of the ablation portion 31 abuts against the inner wall of the LAA 101, thereby ensuring the ablation effect.

The ablation member 1200 may adopt the Joule-Thomson principle, that is, when gas is injected from a higher pressure region into a lower pressure region through a narrow micropore, it will be throttled. The temperature of most of the gas will suddenly decrease after throttling. For example, in some embodiments, local cryoablation of the inner wall of the LAA 101 is performed by injecting gas into the bent tubes 1201 of the ablation member 1200 through micropores at the distal end of a gas delivery tube (not shown) connected to the ablation portion 31 to make the temperature around the bent tubes 1201 suddenly decrease.

With reference to FIGS. 8(a) and 8(b), the catheter portion 32 of the ablation member 1200 includes a plurality of gas inlet tubes 1201a and gas outlet tubes 1201b axially arranged. One gas inlet tube 1201a and one gas outlet tube 1201b are connected to both ends of one bent tube 1201, respectively. The freezing device feeds freezing gas into the bent tube 1201 through the gas inlet tube 1201a, so that during the flow of the freezing gas through the bent tube 1201, local cryoablation is performed on the inner wall of the LAA 101 in contact with the bent tube 1201, and then the gas in the bent tube 1201 is discharged from the body through the gas outlet tube 1201b.

The bent tube 1201, the gas inlet tube 1201a and the gas outlet tube 1201b may be an integrated structure formed by heat-setting a single tube, or after forming the bent tube 1201, the gas inlet tube 1201a and the gas outlet tube 1201b, respectively, the gas inlet tube 1201a and the gas outlet tube 1201b are connected to both ends of the bent tube 1201, and the gas inlet tube 1201a and the gas outlet tube 1201b are communicated with the bent tube 1201.

Further, the bent tubes 1201 are petal-shaped. Referring to the ablation member 1200 shown in FIG. 8(a), the ablation portion 31 of the ablation member 1200 includes six bent tubes 1201. The six bent tubes 1201 are evenly radially arranged around the central axis of the ablation member to form an ablation portion 31 having six petal-like structures without interfering with each other. The ablation portion 31 of this structure can rapidly perform cryoablation by means of the Joule-Thomson principle, and can ensure an ideal effect of freezing.

Referring to FIGS. 8(b) and 9, the gas inlet tube 1201a and the gas outlet tube 1201b communicated with the bent tube 1201 are tied together. Thus, the catheter portion 32 formed by the gas inlet tube 1201a and the gas outlet tube 1201b is easily accommodated in the pushing tube 21. The plurality of gas inlet tubes 1201a and the plurality of gas outlet tubes 1201b may be tied together by means of a sleeve 1202 to make the plurality of gas inlet tubes 1201a and the plurality of gas outlet tubes 1201b more compact and easily accommodated in the pushing tube 21.

In some embodiments, the plurality of gas inlet tubes 1201a are arranged in the vicinity of the central axis of the ablation member 1200, and the plurality of gas outlet tubes 1201b are tubular along the central axis of the ablation member 1200 and located outside the plurality of gas inlet tubes 1201a. With this structural arrangement, the plurality of gas inlet tubes 1201a and the plurality of gas outlet tubes 1201b can be more compactly tied together, and it is convenient to centrally and simultaneously inject cryogen into the plurality of gas inlet tubes 1201a.

Referring to FIG. 9, in an embodiment where the flow blocking membrane 13 is arranged in the sealing portion 11, a disc-shaped ablation portion 31 formed by the plurality of bent tubes 1201 may be pre-placed inside the sealing portion 11 and located on the side where the proximal end of the flow blocking membrane 13 is located, so as to maintain a good occlusion effect of the flow blocking membrane 13.

The ablation portion 31 may be accommodated in the sealing portion 11 via the tube hole 111a of the proximal connector 111 of the sealing portion 11 after being folded. The ablation member 1200 is accommodated in the delivery sheath 22 together with the LAA occluder 10 and delivered into the LAA 101. Upon release of the LAA occluder 10, the bent tubes 1201 are self-expanded and unfolded as the sealing portion 11 is released. The plurality of bent tubes 1201 are formed in a disc shape after being unfolded, and the edges thereof abut against the ostium or neck of the LAA 101. Thus, when the freezing device delivers freezing gas into the bent tube 1201 through the gas inlet tube 1201a, the freezing gas in the bent tube 1201 freezes the inner wall of the LAA 101 in contact with or close to the edge of the bent tube 1201, so as to form an annular isolation band near the ostium or neck of the LAA 101, thereby blocking the conduction of electrical signals between the LAA 101 and the left atrium, achieving the electrical isolation.

Embodiment 4

The same points or similarities between Embodiment 4 and Embodiment 3 will not be described in detail herein, and the main difference therebetween is that the ablation portion 31 including the plurality of petal-shaped bent tubes 1201 and the catheter portion 32 are not integrally arranged, but are two separate assemblies. The catheter portion 32 in the present embodiment is a tubular member that is internally hollow, thereby simplifying the delivery process and reducing the difficulty of delivering an instrument through a curved vessel without significantly affecting the position where the LAA occluder 10 is released.

The ablation portion 31 is fixedly connected to the proximal connector 111 of the sealing portion 11, and the catheter portion 32 is detachably connected to the proximal connector 111. After being unfolded in the sealing portion 11, the ablation portion 31 abuts against the circumferential edge of the sealing portion 11 and forms an annular isolation band on the inner wall of the LAA 101 after cryogen is injected. In an example, ends of each bent tube 1201 are located in the cavity of the proximal connector 111. For example, respective first ends of the plurality of bent tubes 1201 are arranged in the vicinity of the central axis of the proximal connector 111, and respective second ends of the plurality of bent tubes 1201 are fixed onto the inner wall of the proximal connector 111. The first end of each bent tube 1201 is communicated with the cavity of the catheter portion 32, and the second end of each bent tube 1201 is communicated with the cavity of the pushing tube 21, so that the freezing device may inject cryogen into each bent tube 1201 through the catheter portion 32 and via the respective first ends, the cryogen enters the cavity of the pushing tube 21 via the second end after passing through the bent tube 1201, and the cryogen is discharged from the body through the pushing tube 21. The first ends of the plurality of bent tubes 1201 are gathered and fixed together by welding, clamping, binding or bonding. After the first ends of the plurality of bent tubes 1201 are fixed together, an external thread may be provided on an outer surface of the proximal end thereof, and internal threads may be provided on the distal end of the catheter portion 32, so that the catheter portion 32 may be detachably connected to the proximal end of the ablation portion 31 by means of threads. Since the ablation portion 31 is fixedly connected to the proximal connector 111, the detachable connection between the catheter portion 32 and the proximal connector 111 is achieved.

Further, the respective first ends of the plurality of bent tubes 1201 are accommodated in a sleeve. That is, the respective first ends of the plurality of bent tubes 1201 are fixed together by a sleeve. External threads may be provided on the sleeve, and internal threads may be provided on the distal end of the catheter portion 32, whereby the catheter portion 32 may be connected to the sleeve by means of threads to achieve the detachable connection between the catheter portion 32 and the proximal end of the ablation portion 31. Since the ablation portion 31 is fixedly connected to the proximal connector 111, the detachable connection between the catheter portion 32 and the proximal connector 111 is achieved.

During delivery of the LAA occluder 10, the catheter portion 32 may be connected to the proximal connector 111 of the sealing portion 11 and accommodated in the cavity of the pushing tube 21. After the pushing tube 21 and the proximal connector 111 are also connected, the catheter portion 32 is delivered to the LAA 101 in the delivery sheath 22 together with the LAA occluder 10. In another embodiment, rather than the catheter portion 32 being delivered to the LAA 101 in the delivery sheath 22 together with the LAA occluder 10, the distal end of the catheter portion 32 extends from the proximal end of a delivery tube into the cavity of the delivery tube after the LAA occluder 10 is unfolded in the LAA 101, and the catheter portion 32 is then delivered to the LAA 101 along the delivery tube. After the distal end of the catheter portion 32 is connected to the proximal connector 111 and the freezing device is connected to the proximal end of the catheter portion 32, the freezing device injects cryogen into the ablation portion 31 through the catheter portion 32.

Embodiment 5

Figure 10:
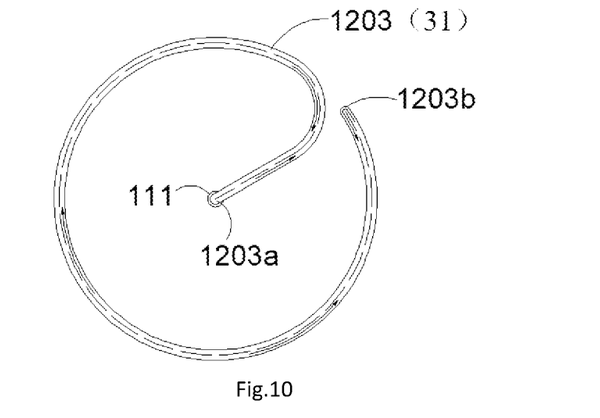
FIG. 10 is a top view of one structure of an ablation portion in an occluding system of Embodiment 5 after being unfolded.
Figure 11:
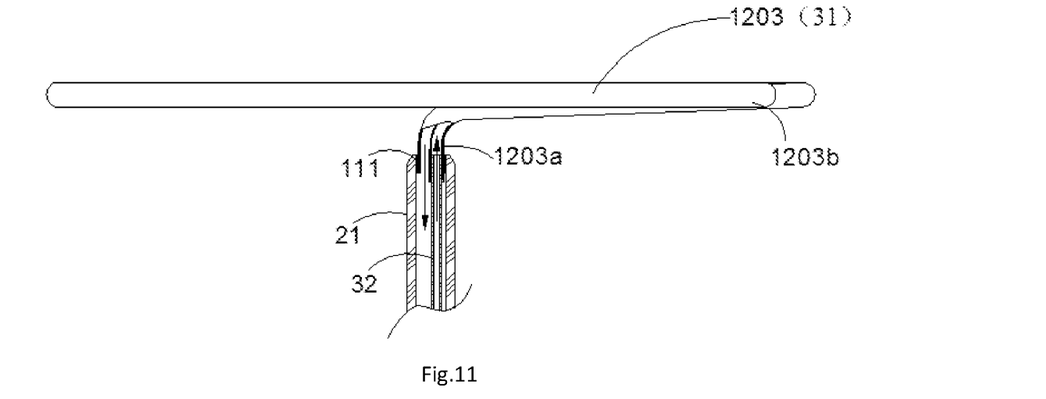
FIG. 11 is a schematic view of the ablation portion in FIG. 10 connected to a catheter portion by a proximal connector.

The same points or similarities between Embodiment 5 and Embodiment 4 will not be described in detail herein, and the main difference therebetween is that, referring to FIGS. 10 and 11, in Embodiment 5, the ablation portion 31 includes a double-cavity bent tube 1203, and the bent tube 1203 is annular after being unfolded and abuts against the circumferential edge of the sealing portion 11, so as to form an annular isolation band on the inner wall of the LAA 101 after injecting cryogen. The first end portion 1203a of the bent tube 1203 has two openings, one of which is used to inject cryogen after being connected to the catheter portion 32, and the other of which is used to discharge cryogen after flowing along the bent tube 1203. The ablation portion 31 includes only one bent tube, so that when the ablation portion 31 is folded in the sealing portion 11, the outer diameter of the sealing portion 11 in a compressed state is not excessively increased, and it is more likely to fold.

In one implementation, a partition (not shown) extending along its length direction is arranged inside the bent tube 1203, thereby dividing the interior of the bent tube 1203 into two cavities. With continued reference to FIGS. 10 and 11, the two cavities of the bent tube 1203 are arranged side by side along the length direction of the bent tube 1203, the second end 1203b of the bent tube 1203 is closed, and the two cavities of the bent tube 1203 are communicated near the second end 1203b. The first end 1203a of the bent tube 1203 is fixed onto the inner wall of the proximal connector 111. Internal threads may be provided at the position of a first opening of the bent tube 1203, external threads may be provided on the catheter portion 32, and the catheter portion 32 is in threaded connection with the first end 1203a of the bent tube 1203. The second end 1203b of the bent tube 1203 may be a free end or may be fixed to the distal end of the sealing portion 11 as long as the total length of the bent tube 1203 is not greater than the length of the sealing portion 11 in a compressed state. The second end 1203b of the bent tube 1203 is fixed to the distal end of the sealing portion 11, and when the sealing portion 11 needs to be accommodated in the delivery sheath 22, the bent tube 1203 can be rapidly folded along with the compression of the sealing portion 11 without affecting the transition of the sealing portion 11 from an unfolded state to a compressed state. When the sealing portion 11 is accommodated in the delivery sheath 22, the bent tube 1203 may be folded in an approximately straight line shape as the sealing portion 11 is compressed.

In an example, after the proximal end of the catheter portion 32 is connected to the freezing device, the freezing device injects cryogen into the first opening of the first end 1203a of the bent tube 1203 through the catheter portion 32. The cryogen moves from the first opening along one of the cavities of the bent tube 1203 towards the second end 1203b of the bent tube 1203 and enters the other cavity where the two cavities are communicated, then moves along the bent tube 1203 towards the first end 1203a of the bent tube 1203, is discharged from the second opening into the pushing tube 21, and is finally discharged from the body via the pushing tube 21. Arrows in FIGS. 10 and 11 indicate the moving direction of cryogen.

Figure 12:
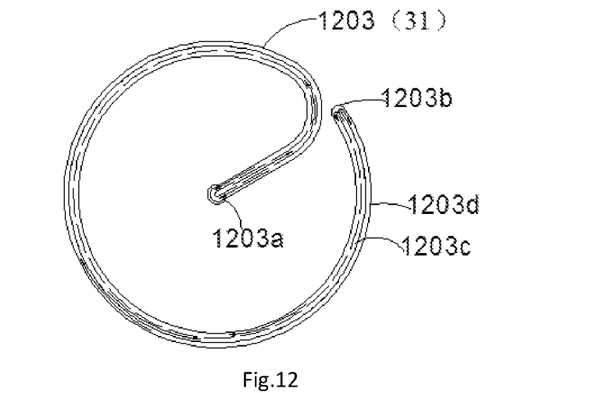
FIG. 12 is a top view of another structure of the ablation portion in the occluding system of Embodiment 5 after being unfolded.
Figure 13:
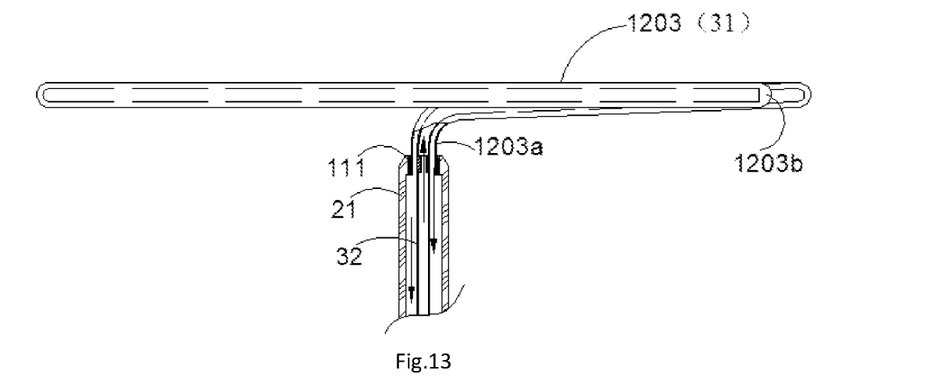
FIG. 13 is a schematic view of the ablation portion in FIG. 12 connected to a catheter portion by a proximal connector.

In another implementation, referring to FIGS. 12 and 13, the bent tube 1203 includes a sleeved inner tube 1203c and outer tube 1203d, and the inner tube 1203c and the outer tube 1203d are connected by a partition (not shown). The interior of the inner tube 1203c is hollow and defines the first cavity of bent tube 1203, and a cavity between the outer tube 1203d and the inner tube 1203c is the second cavity of the bent tube 1203. Referring to FIG. 13, at the first end 1203a of the bent tube 1203, internal threads are provided in the inner tube 1203c, and the inner tube 1203c may be detachably connected to the catheter portion 32 by means of threads at the first end 1203a of the bent tube 1203. At the second end 1203b of the bent tube 1203, an end of the outer tube 1203d is closed and constitutes the second end 1203b of the bent tube 1203, and an end of the inner tube 1203c is located inside the outer tube 1203d, whereby the first cavity is communicated with the second cavity at the second end 1203b of the bent tube 1203. When the inner tube 1203c is connected to the catheter portion 32, the cryogen injected into the first cavity through the catheter portion 32 moves along the inner tube 1203c, enters the second cavity at the second end 1203b of the bent tube 1203, then moves along the outer tube 1203d towards the first end 1203a of the bent tube 1203, is discharged into the pushing tube 21 via an opening between the inner tube 1203c and the outer tube 1203d at the first end 1203a of the bent tube 1203, and is finally discharged from the body along the pushing tube 21.

In another embodiment, the ablation portion 31 includes a single-cavity bent tube which is open at both ends, and the bent tube is annular after being unfolded and abuts against the circumferential edge of the sealing portion 11, so as to form an annular isolation band on the inner wall of the LAA 101 after injecting cryogen. The first end of the bent tube is located in the cavity of the proximal connector 111, may be suspended in the cavity of the proximal connector 111, or may be fixed onto the inner wall of the proximal connector 111. The second end of the bent tube is fixed onto the inner wall of the proximal connector 111. The first end of the bent tube may be detachably connected to the distal end of the catheter portion 32 by means of threaded or clamping connection, etc. And after the proximal end of the catheter portion 32 is connected to the freezing device, the freezing device injects cryogen into the ablation portion 31, i.e. the bent tube, through the catheter portion 32. The cryogen moves along the bent tube towards the second end thereof, is discharged through an opening at the second end into the pushing tube 21, and is finally discharged from the body via the pushing tube 21.

Each feature of the above-described embodiments can be combined in any combination, and in order to make the description concise, not all the possible combinations of each feature in the above-described embodiments are described. However, as long as there is no contradiction between the combinations of these features, they should be considered as within the scope of the embodiments.

The above-described embodiments express only a few implementations, which are described in greater detail but should not be construed as limiting the scope. It will be appreciated by those of ordinary skill in the art that numerous variations and modifications may be made to the embodiments without departing from their scope.

The invention claimed is:

1. A left atrial appendage (LAA) occluder, comprising:
a fixing portion,
a sealing portion that is disc-shaped and internally hollow, the sealing portion being located on a proximal side of the fixing portion and connected to a proximal end of the fixing portion;
an ablation portion arranged in an interior space of the sealing portion, and
a hollow proximal connector arranged at a proximal end of the sealing portion,
wherein the ablation portion is connected to the proximal connector, the ablation portion is configured to freeze an LAA after being injected with cryogen so as to form an annular isolation band on an inner wall of the LAA, the annular isolation band is configured to block the conduction of electrical signals between the LAA and a left atrium, when the sealing portion is in a compressed state, the ablation portion is folded and accommodated in the sealing portion, and the ablation portion abuts against a circumferential edge of the sealing portion after being unfolded in the sealing portion; and
wherein the ablation portion comprises a double-cavity bent tube which is unfolded to be annular and abuts against a proximal wall of the sealing portion, one end of the double-cavity bent tube is fixed on to an inner wall of the hollow proximal connector, and the end of the double-cavity bent tube has two openings that are configured to inject and discharge cryogen respectively.

2. The LAA occluder according to claim 1, wherein at least one flow blocking membrane is arranged in the sealing portion and located on a side where a distal end of the ablation portion is located.

3. The LAA occluder according to claim 1, wherein the double-cavity bent tube comprises a first end, a second end, and two cavities, the first end is fixed to the inner wall of the hollow proximal connector, the second end is closed, and the two cavities are in communication near the second end.

4. The LAA occluder according to claim 1, where in the double-cavity bent tube comprises a single bent tube.

5. The LAA occluder according to claim 1, wherein the double-cavity bent tube comprise an inner tube and an outer tube, the outer tube is sleeved on the inner tube, a first cavity is defined in an interior of the inner tube, and a second cavity is defined between the inner tube and the outer tube.

6. An occluding system, comprising:
a left atrial appendage (LAA) occluder, a pushing tube, a delivery sheath, and an ablation member,
wherein the LAA occluder comprises a sealing portion and a fixing portion connected with the sealing portion, the sealing portion being located on a proximal side of the fixing portion and connected to a proximal end of the fixing portion,
the sealing portion is disc-shaped, internally hollow, and has an opening at a proximal end, a hollow proximal connector is located at the opening, the pushing tube is movably arranged in the delivery sheath and detachably connected to the hollow proximal connector at the proximal end of the sealing portion,
the ablation member comprises an ablation portion, the ablation member comprising the ablation portion is accommodated in the sealing portion of the LAA occluder, and in a delivery state, the LAA occluder accommodating the ablation member is accommodated in the delivery sheath,
the ablation portion against a proximal wall of the sealing portion after being unfolded in the sealing portion, after the LAA occluder is unfolded in an LAA, the ablation portion is configured to freeze the LAA after being injected with cryogen so as to form an annular isolation band on an inner wall of the LAA, and the annular isolation band is configured to block the conduction of electrical signals between the LAA and a left atrium; and
wherein the ablation portion comprises a double-cavity bent tube which is unfolded to be annular and abuts against the circumferential edge of the sealing portion, one end of the double-cavity bent tube is fixed on to an inner wall of the hollow proximal connector, and the end of the double-cavity bent tube has two openings that are configured to inject and discharge cryogen respectively.

7. The occluding system according to claim 6, wherein the ablation member further comprises a catheter portion, one end of the catheter portion is connected to the ablation portion, the catheter portion is detachably connected to the proximal end of the sealing portion, and the interior of the catheter portion is communicated with the proximal end opening of the sealing portion.

8. The occluding system according to claim 7, wherein the pushing tube is internally hollow and the catheter portion is located in the pushing tube at least during ablation; or, the catheter portion is the pushing tube.

9. The occluding system according to claim 6, wherein at least one flow blocking membrane is arranged in the sealing portion and located on a side where a distal end of the ablation portion is located.

10. The occluding system according to claim 6, wherein the distal end of the catheter portion has a tapered section, an inner diameter of a distal end of the tapered section being smaller than an inner diameter of a proximal end of the tapered section.

11. The occluding system according to claim 6, wherein the double-cavity bent tube comprises a first end, a second end, and two cavities, the first end is fixed to the inner wall of the hollow proximal connector, the second end is closed, and the two cavities are in communication near the second end.

12. The occluding system according to claim 6, wherein the double-cavity bent tube comprises a single bent tube.

13. The occluding system according to claim 6, wherein the double-cavity bent tube comprises an inner tube and an outer tube, the outer tube is sleeved on the inner tube, a first cavity is defined in an interior of the inner tube, and a second cavity is defined between the inner tube and the outer tube.

* * * * *